(12) United States Patent
Gururaj et al.

(10) Patent No.: US 9,220,901 B2
(45) Date of Patent: Dec. 29, 2015

(54) NEUROSTIMULATION SYSTEM FOR PREVENTING MAGNETICALLY INDUCED CURRENTS IN ELECTRONIC CIRCUITRY

(71) Applicant: BOSTON SCIENTIFIC NEUROMODULATION CORPORATION, Valencia, CA (US)

(72) Inventors: Kiran Gururaj, Valencia, CA (US); Pujitha Weerakoon, Valencia, CA (US); Goran N. Marnfeldt, Valencia, CA (US); Jordi Parramon, Valencia, CA (US); Salomo Murtonen, Pasadena, CA (US); Emanuel Feldman, Simi Valley, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/801,596

(22) Filed: Mar. 13, 2013

(65) Prior Publication Data

US 2013/0245723 A1 Sep. 19, 2013

Related U.S. Application Data

(60) Provisional application No. 61/612,241, filed on Mar. 16, 2012.

(51) Int. Cl.
*A61N 1/36* (2006.01)
*A61N 1/08* (2006.01)

(52) U.S. Cl.
CPC .............. *A61N 1/36142* (2013.01); *A61N 1/08* (2013.01); *A61N 1/36* (2013.01); *A61N 1/3605* (2013.01); *A61N 2001/086* (2013.01)

(58) Field of Classification Search
CPC ......... A61N 1/08; A61N 1/36; A61N 1/3605; A61N 1/36142; A61N 2001/086
USPC ............................................... 607/61, 62, 116
See application file for complete search history.

(56) References Cited

U.S. PATENT DOCUMENTS 4,548,208 A * 10/1985 Niemi .............................. 600/14
5,671,179 A * 9/1997 Javanifard ................. 365/185.33
5,702,431 A * 12/1997 Wang et al. ...................... 607/61

(Continued)

OTHER PUBLICATIONS

PCT International Search Report for PCT/US2013/031015, Applicant: Boston Scientific Neuromodulation Corporation, Form PCT/ISA/210 and 220, dated Jun. 19, 2013 (6pages).

(Continued)

*Primary Examiner* — Christopher A Flory
(74) *Attorney, Agent, or Firm* — Lowe Graham Jones PLLC; Bruce E. Black

(57) ABSTRACT

A neurostimulation device capable of being placed between an active stimulation state and an inactive stimulation state and method of using same. The neurostimulation device comprises a plurality of electrical terminals configured for being respectively coupled to a plurality of stimulation electrodes, a first solid-state switching device coupled to a first one of the electrical terminals, a variable power source coupled to the first switching device, and a controller configured for, when the neurostimulation device is in the inactive stimulation state, prompting the variable power source to selectively output a relatively low voltage to place the first switching device into a first open state and a relatively high voltage to place the first switching device into a second open state.

24 Claims, 9 Drawing Sheets

(56) References Cited

U.S. PATENT DOCUMENTS

| | | |
|---|---|---|
| 6,185,461 B1 | 2/2001 | Er |
| 6,516,227 B1 | 2/2003 | Meadows et al. |
| 6,895,280 B2 | 5/2005 | Meadows et al. |
| 7,359,751 B1* | 4/2008 | Erickson et al. ............... 607/27 |
| 7,539,538 B2 | 5/2009 | Parramon et al. |
| 7,571,007 B2* | 8/2009 | Erickson et al. ............... 607/61 |
| 7,650,184 B2 | 1/2010 | Walter |
| 7,715,911 B2* | 5/2010 | Vernon et al. ................. 607/2 |
| 7,937,158 B2* | 5/2011 | Erickson et al. ............... 607/59 |
| 8,019,439 B2 | 9/2011 | Kuzma et al. |
| 8,249,701 B2* | 8/2012 | Imran et al. ................... 607/2 |
| 8,258,766 B1* | 9/2012 | Sutardja ....................... 323/282 |
| 8,494,626 B2* | 7/2013 | Moffitt et al. ................. 607/2 |
| 8,538,538 B2* | 9/2013 | Goetz et al. ................... 607/45 |
| 8,543,202 B2* | 9/2013 | Goetz et al. ................... 607/9 |
| 8,560,081 B2* | 10/2013 | Cilingiroglu ................... 607/61 |
| 8,571,677 B2* | 10/2013 | Torgerson et al. ............. 607/59 |
| 8,583,249 B2* | 11/2013 | Pillai et al. .................... 607/59 |
| 8,588,927 B2* | 11/2013 | Roy et al. ....................... 607/62 |
| 2002/0010414 A1* | 1/2002 | Coston et al. ................. 604/20 |
| 2003/0139781 A1 | 7/2003 | Bradley et al. |
| 2003/0204224 A1 | 10/2003 | Torgerson et al. |
| 2005/0010265 A1* | 1/2005 | Baru Fassio et al. .......... 607/48 |
| 2005/0267546 A1 | 12/2005 | Parramon et al. |
| 2006/0004424 A1* | 1/2006 | Loeb et al. ..................... 607/63 |
| 2006/0031378 A1* | 2/2006 | Vallapureddy et al. ....... 709/208 |
| 2006/0206162 A1 | 9/2006 | Wahlstrand et al. |
| 2007/0150036 A1 | 6/2007 | Anderson |
| 2007/0168004 A1 | 7/2007 | Walter |
| 2007/0168007 A1 | 7/2007 | Kuzma et al. |
| 2007/0265639 A1* | 11/2007 | Danek et al. ................... 606/130 |
| 2008/0243210 A1 | 10/2008 | Doron et al. |
| 2009/0082691 A1* | 3/2009 | Denison ............. A61B 5/04004 600/544 |
| 2009/0163980 A1 | 6/2009 | Stevenson |
| 2009/0207939 A1* | 8/2009 | Mertens et al. ................ 375/297 |
| 2009/0312808 A1* | 12/2009 | Tyler et al. ..................... 607/2 |
| 2010/0010559 A1 | 1/2010 | Zhang et al. |
| 2010/0069997 A1* | 3/2010 | Dupeyron .......... A61N 1/36032 607/57 |
| 2010/0076524 A1 | 3/2010 | Forsberg et al. |
| 2010/0106219 A1* | 4/2010 | Torgerson et al. ............. 607/59 |
| 2010/0106231 A1* | 4/2010 | Torgerson et al. ............. 607/116 |
| 2010/0114248 A1 | 5/2010 | Donofrio et al. |
| 2010/0152817 A1* | 6/2010 | Gillbe ................. A61N 1/0551 607/72 |
| 2010/0280577 A1* | 11/2010 | Roy et al. ....................... 607/62 |
| 2011/0093043 A1* | 4/2011 | Torgerson ............ A61N 1/0531 607/59 |
| 2011/0101914 A1* | 5/2011 | Niessen et al. ................ 320/107 |
| 2011/0125214 A1* | 5/2011 | Goetz ................ A61N 1/36017 607/45 |
| 2011/0187339 A1* | 8/2011 | Trattler et al. ................. 323/283 |
| 2011/0264171 A1* | 10/2011 | Torgerson ....................... 607/59 |
| 2011/0270357 A1* | 11/2011 | Torgerson .......... A61N 1/36082 607/59 |
| 2012/0185018 A1* | 7/2012 | Cilingiroglu ................... 607/65 |
| 2012/0238855 A1* | 9/2012 | Lanning et al. ................ 600/378 |
| 2012/0277822 A1* | 11/2012 | Trier .................. A61N 1/36071 607/46 |
| 2013/0073008 A1* | 3/2013 | Ternes ............... A61N 1/36153 607/62 |
| 2013/0310894 A1* | 11/2013 | Trier .................. A61N 1/36071 607/59 |
| 2013/0325085 A1* | 12/2013 | Carbunaru et al. ............. 607/62 |

OTHER PUBLICATIONS

PCT Written Opinion of the International Search Authority for PCT/US2013/03105, Applicant: Boston Scientific Neuromodulation Corporation, Form PCT/ISA/237, dated Jun. 19, 2013 (7pages).

* cited by examiner

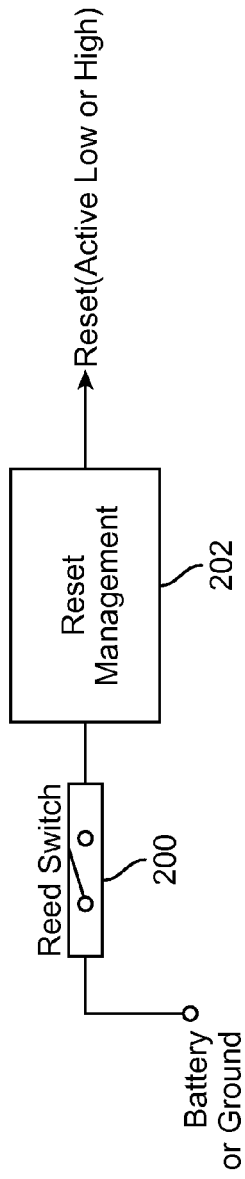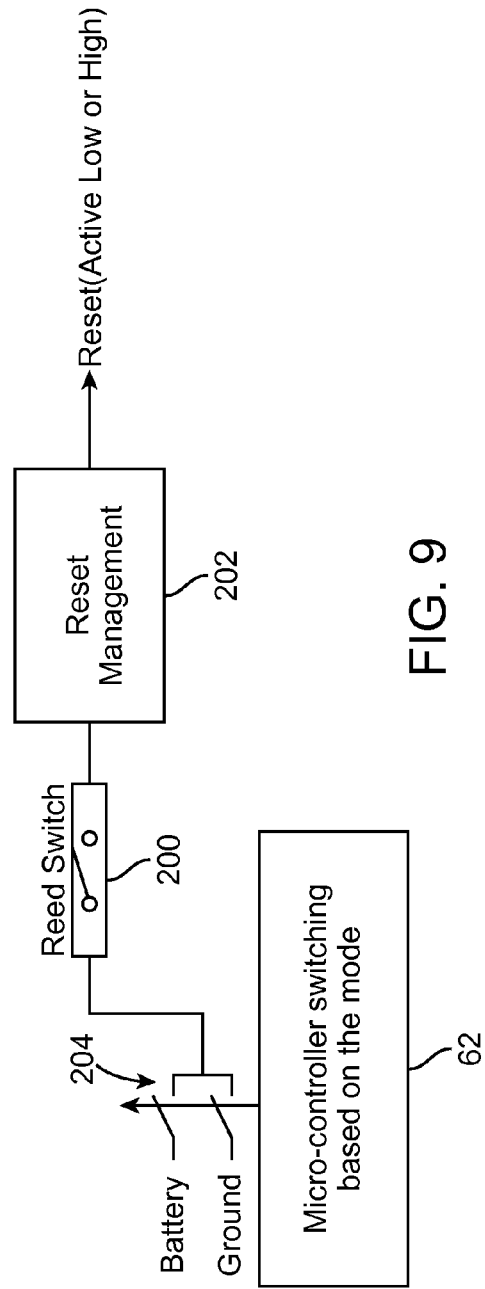

NEUROSTIMULATION SYSTEM FOR PREVENTING MAGNETICALLY INDUCED CURRENTS IN ELECTRONIC CIRCUITRY

RELATED APPLICATION DATA

The present application claims the benefit under 35 U.S.C. §119 to U.S. provisional patent application Ser. No. 61/612,241, filed Mar. 16, 2012. The foregoing application is hereby incorporated by reference into the present application in its entirety.

FIELD OF THE INVENTION

The present invention relates to tissue stimulation systems.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes at least one stimulation lead implanted at the desired stimulation site and an Implantable Pulse Generator (IPG) implanted remotely from the stimulation site, but coupled either directly to the stimulation lead(s) or indirectly to the stimulation lead(s) via one or more lead extensions. Thus, electrical pulses can be delivered from the neurostimulator to the electrodes carried by the stimulation lead(s) to stimulate or activate a volume of tissue in accordance with a set of stimulation parameters and provide the desired efficacious therapy to the patient. A typical stimulation parameter set may include the electrodes that are sourcing (anodes) or returning (cathodes) the stimulation current at any given time, as well as the amplitude, duration, rate, and burst rate of the stimulation pulses. Significant to the present inventions described herein, a typical IPG may be manually inactivated by the patient by placing a magnet over the implanted IPG, which closes a reed switch contained within the IPG.

The neurostimulation system may further comprise a handheld Remote Control (RC) to remotely instruct the neurostimulator to generate electrical stimulation pulses in accordance with selected stimulation parameters. The RC may, itself, be programmed by a technician attending the patient, for example, by using a Clinician's Programmer (CP), which typically includes a general purpose computer, such as a laptop, with a programming software package installed thereon.

Electrical stimulation energy may be delivered from the neurostimulator to the electrodes using one or more current-controlled sources for providing stimulation pulses of a specified and known current (i.e., current regulated output pulses), or one or more voltage-controlled sources for providing stimulation pulses of a specified and known voltage (i.e., voltage regulated output pulses). The circuitry of the neurostimulator may also include voltage converters, power regulators, output coupling capacitors, and other elements as needed to produce constant voltage or constant current stimulus pulses.

The electrical stimulation energy may be delivered between a specified group of electrodes as monophasic electrical energy or multiphasic electrical energy. Monophasic electrical energy includes a series of pulses that are either all negative (cathodic), or alternatively all positive (anodic). Multiphasic electrical energy includes a series of pulses that alternate between positive and negative.

For example, multiphasic electrical energy may include a series of biphasic pulses, with each biphasic pulse including a cathodic (negative) stimulation pulse (during a first phase) and an anodic (positive) charge recovery pulse (during a second phase) that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the charge recovery pulse).

The second phase may have an active charge recovery pulse, wherein electrical current is actively conveyed through the electrode via current or voltage sources, and/or a passive charge recovery pulse, wherein electrical current is passively conveyed through the electrode via redistribution of the charge flowing from coupling capacitances present in the circuit, while the current or voltage sources are turned off. In the case of passive charge recovery, switches associated with the active electrodes are closed in order to passively convey the charge to AC ground.

Neurostimulation systems, which may not be limited to SCS used to treat chronic pain, are routinely implanted in patients who are in need of Magnetic Resonance Imaging (MRI). Thus, when designing implantable neurostimulation systems, consideration must be given to the possibility that the patient in which neurostimulator is implanted may be subjected to electro-magnetic forces generated by MRI scanners, which may potentially cause damage to the neurostimulator as well as discomfort to the patient.

In particular, in MRI, spatial encoding relies on successively applying magnetic field gradients. The magnetic field strength is a function of position and time with the application of gradient fields throughout the imaging process. Gradient fields typically switch gradient coils (or magnets) ON and OFF thousands of times in the acquisition of a single image in the present of a large static magnetic field. Present-day MRI scanners can have maximum gradient strengths of 100 mT/m and much faster switching times (slew rates) of 150 mT/m/ms, which is comparable to stimulation therapy frequencies. Typical MRI scanners create gradient fields in the range of 100 Hz to 30 KHz, and radio frequency (RF) fields of 64 MHz for a 1.5 Tesla scanner and 128 MHz for a 3 Tesla scanner.

Despite the fact that an IPG implanted within a patient undergoing an MRI will be automatically deactivated (i.e., the magnetic field present in the MRI scanner will, via closing of the reed switch, automatically deactivate a IPG), the strength of the gradient magnetic field may be high enough to induce voltages (5-10 Volts depending on the orientation of the lead inside the body with respect to the MRI scanner) on to the stimulation lead(s), which in turn, are seen by the IPG electronics. If these induced voltages are higher than the voltage supply rails of the IPG electronics, there could exist paths within the IPG that could induce current through the electrodes on the stimulation lead(s), which in turn, could cause unwanted stimulation to the patient due to the similar frequency band, between the MRI-generated gradient field and intended stimulation energy frequencies for therapy, as well as potentially damaging the electronics within the IPG. To elaborate further, the gradient (magnetic) field may induce electrical energy within the wires of the stimulation lead(s), which may be conveyed into the circuitry of the IPG and then out to the electrodes of the stimulation leads via the passive charge recovery switches. For example, in a conventional neurostimulation system, an induced voltage at the connector of the IPG that is higher than IPG battery voltage (~4-5V), may induce such unwanted stimulation currents. RF energy generated by the MRI scanner may induce electrical currents of even higher voltages within the IPG.

Typically, any electrical current blocking techniques, such as adding filters within the IPG, must be custom designed to suit a particular IPG. There, thus, remains a need to block electrical currents induced within the IPG via external means, such as MRI, with minimal modifications to the IPG.

SUMMARY OF THE INVENTION

In accordance with a first aspect of the present inventions, a neurostimulation device capable of being placed between an active stimulation state and an inactive stimulation state is provided. The neurostimulation device comprises a plurality of electrical terminals configured for being respectively coupled to a plurality of stimulation electrodes, and a first solid-state switching device coupled to a first one of the electrical terminals. In one embodiment, each of the first and second switching devices comprises two complementary transmission gate switches (e.g., an N-channel metal-oxide semiconductor (NMOS) transistor and a P-channel metal-oxide semiconductor transistor (PMOS)).

The neurostimulation device further comprises a variable power source coupled to the first switching device, and a controller configured for, when the neurostimulation device is in the inactive stimulation state, prompting the variable power source to selectively output a relatively low voltage (e.g., less than five volts) to place the first switching device into a first open state and a relatively high voltage (e.g., greater than ten volts) to place the first switching device into a second open state. The controller may be further configured for prompting the variable power source to output the relatively high voltage to place the first switching device into the second open state when the neurostimulation is in the active stimulation state. The variable power supply may comprise a battery configured for outputting the relatively low voltage, and a high voltage circuit configured for outputting the relatively high voltage.

In one embodiment, the neurostimulation device further comprises a second solid-state switching device coupled to a second one of the electrical terminals, with the first and second switching devices being shorted to each other. In this case, the variable power source is coupled to the second switching device, and the controller is configured for, when the neurostimulation device is in the inactive stimulation state, prompting the variable power source to selectively output the relatively low voltage to place the second switching device into the first open state and the relatively high voltage to place the second switching device into the second open state.

In this embodiment, the neurostimulation device may further comprise at least one stimulation source, in which case, the controller may be configured for prompting the stimulation source(s) to convey a series of stimulation pulses between the first and second electrical terminals when the neurostimulation device is in the active stimulation state, and for prompting the variable power source to output the relatively high voltage during the conveyance of each of the pulses, and to ground the first switch after the conveyance of each of the pulses to place the first switching device into a closed state.

In an optional embodiment, the neurostimulation device further comprises telemetry circuitry configured for receiving a signal external to the neurostimulation device, in which case, the controller may be configured for prompting the variable power source to output the relatively high voltage in response to the external signal. The neurostimulation device may further comprise a sensing mechanism configured for deactivating the neurostimulation device in the presence of an external magnetic field, such that the controller, in response to the external signal, may be configured for preventing the neurostimulation device from being deactivated; for example, by disabling the sensing mechanism.

In accordance with a second aspect of the present inventions, a method of preventing induced electrical current in a neurostimulation device associated with a patient (e.g., by being implanted within the patient) exposed to external energy is provided. The neurostimulation device includes a first solid-state switching device coupled to a first stimulation electrode via a first electrical terminal. The first stimulation electrode may be carried by a stimulation lead coupled to neurostimulation device. The method comprises placing the neurostimulation device in an inactive stimulation state, applying a relatively low voltage (e.g., less than five volts) to the first switching device when the neurostimulation device is in the inactive stimulation state, thereby placing the first switching device in a first open state, applying a relatively high voltage (e.g., greater than ten volts) to the second switching device when the neurostimulation device is in the inactive stimulation state, thereby placing the first switching device in a second open state, and applying the external energy (e.g., magnetic energy, such as a gradient magnetic field generated by a magnetic resonance imaging (MRI) scanner) to the patient, thereby inducing a voltage on the first electrical terminal. The induced voltage is at a level that is prevented from conducting current through the first switching device when in the second open state that would otherwise be conducted through the first switching device when in the first open state.

In one embodiment, the neurostimulation device includes a second solid-state switching device coupled to a second stimulation electrode via a second electrical terminal, in which case, the method may further comprise applying the relatively low voltage to the second switching device when the neurostimulation device is in the inactive stimulation state, thereby placing the second switching device in a first open state, applying the relatively high voltage to the second switching device when the neurostimulation device is in the inactive stimulation state, thereby placing the second switching device in a second open state, and applying the external energy to the patient, thereby inducing a voltage on the second electrical terminal. The induced voltage is at a level that is prevented from conducting current through the second switching device when in the second open state that would otherwise be conducted through the second switching device when in the first open state. In this case, the method may further comprise conveying a series of stimulation pulses between the first and second electrode via the first and second electrical terminals, thereby creating a charge in tissue adjacent the first electrode, wherein the relatively high voltage is applied to the first and second switching devices during the conveyance of each of the pulses, and the first and second switching devices are grounded to place the first and second switching devices into a closed state after the conveyance of each of the pulses, thereby recovering the charge from the tissue.

An optional method comprises transmitting a signal to the neurostimulation device, wherein the relatively high voltage is applied to the first switching device in response to the transmitted signal. The method may further comprise, in response to the signal, preventing the neurostimulation device from being deactivated in the presence of the external energy. For example, if the neurostimulation device includes a sensing mechanism configured for inactivating the neurostimulation device in the presence of the external energy, the neurostimulation device may be prevented from being deactivated by disabling the sensing mechanism.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 8 is a block diagram of a prior art IPG reset management circuit;

FIG. 9 is a block diagram a reset management circuit used in the IPG of FIG. 5.

DETAILED DESCRIPTION OF THE EMBODIMENTS

The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
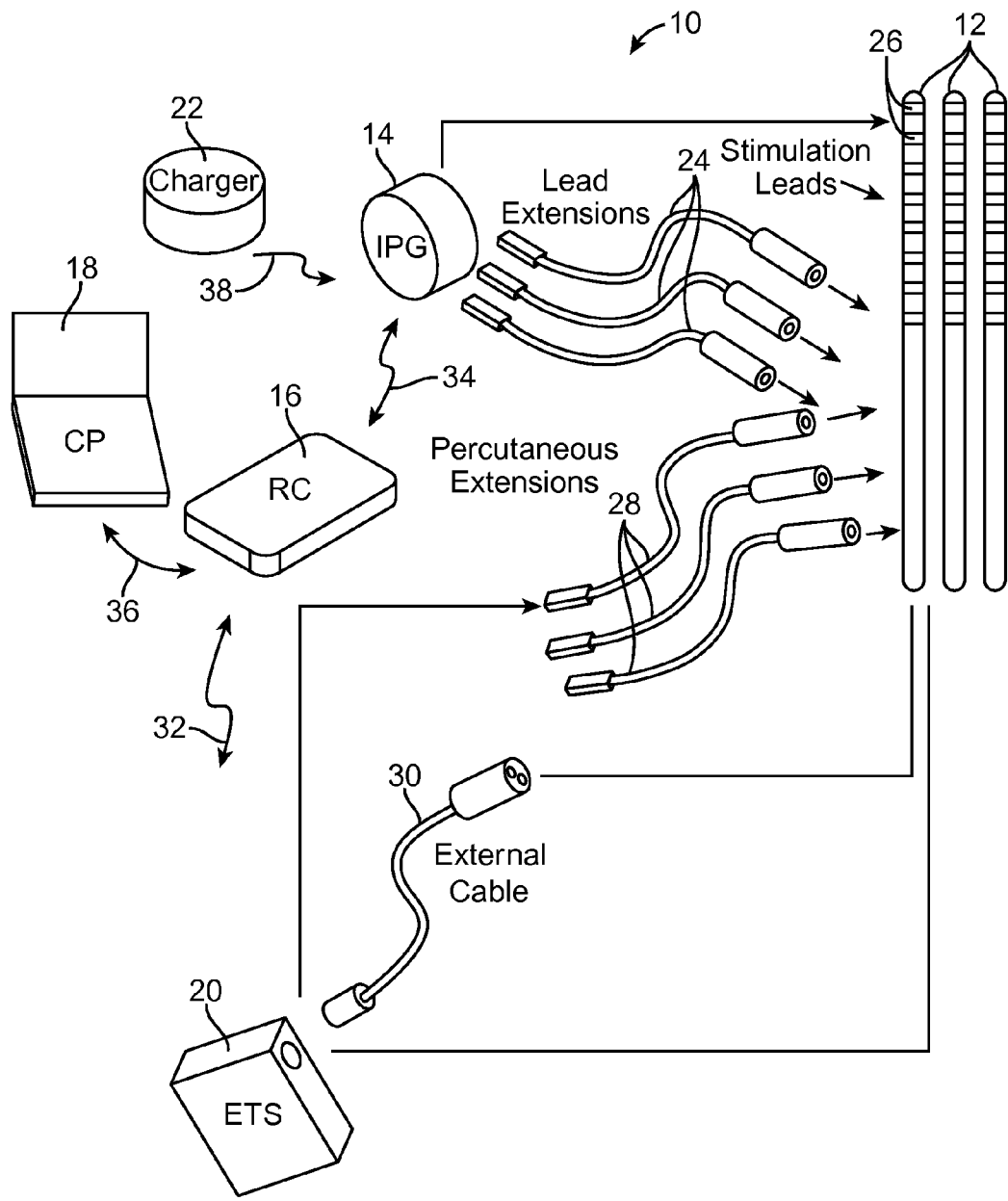
FIG. 1 is a plan view of a Spinal Cord Stimulation (SCS) system constructed in accordance with one embodiment of the present inventions.

Turning first to FIG. 1, an exemplary spinal cord stimulation (SCS) system 10 generally includes one or more (in this case, three) implantable stimulation leads 12, a pulse generating device in the form of an implantable pulse generator (IPG) 14, an external control device in the form of a remote controller RC 16, a clinician's programmer (CP) 18, an external trial stimulator (ETS) 20, and an external charger 22.

The IPG 14 is physically connected via one or more lead extensions 24 to the stimulation leads 12, which carry a plurality of electrodes 26 arranged in an array. The stimulation leads 12 are illustrated as percutaneous leads in FIG. 1, although as will be described in further detail below, a surgical paddle lead can be used in place of the percutaneous leads. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 2:
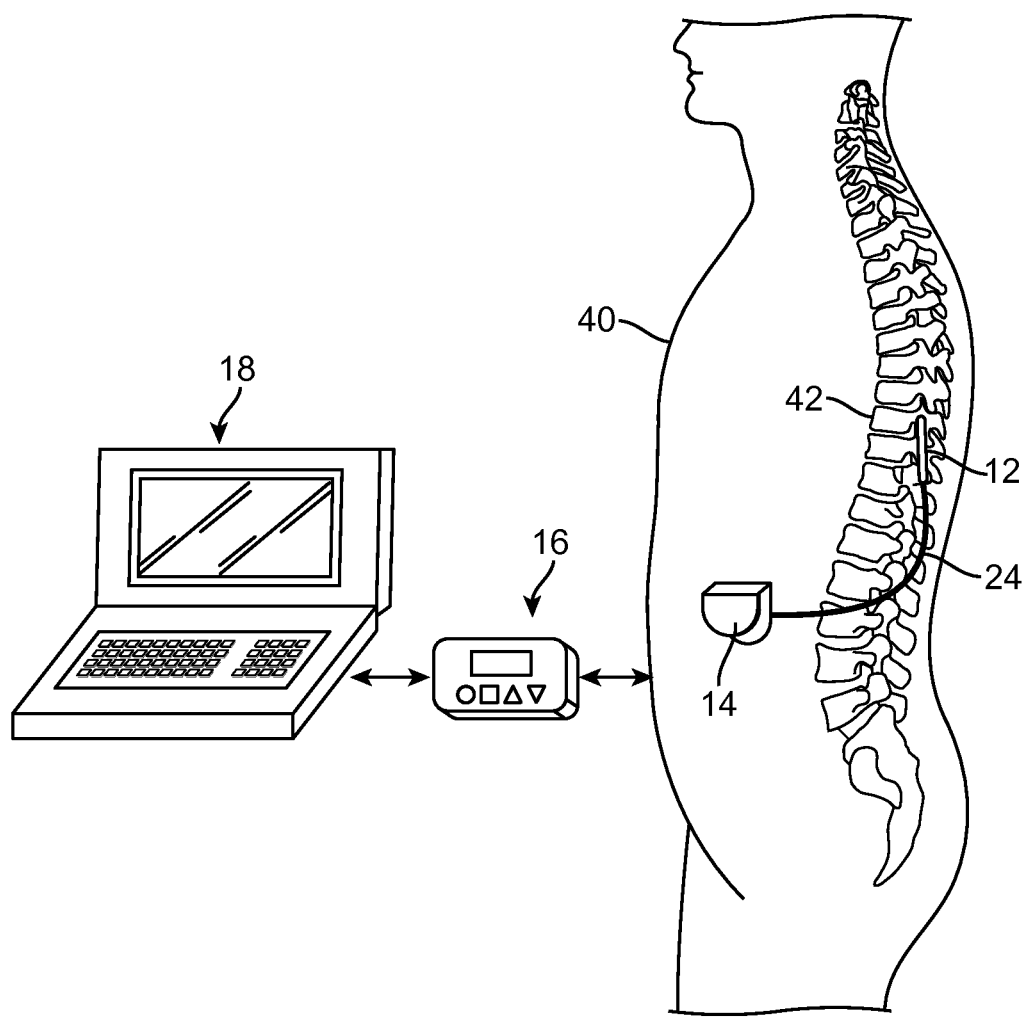
FIG. 2 is a plan view of the SCS system of FIG. 1 in use within a patient.

As shown in FIG. 2, the stimulation leads 12 are implanted within the spinal column 42 of a patient 40. The preferred placement of the electrode leads 12 is adjacent, i.e., resting near, the spinal cord area to be stimulated. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the electrode leads 12. As there shown, the CP 18 communicates with the IPG 14 via the RC 16.

Figure 3:
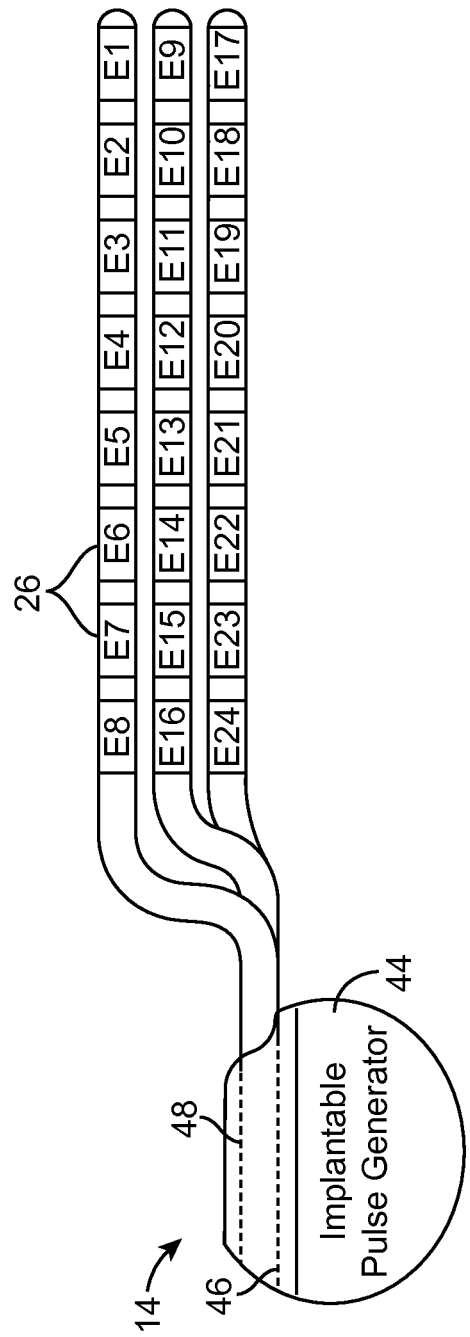
FIG. 3 is a plan view of an implantable pulse generator (IPG) and three percutaneous stimulation leads used in the SCS system of FIG. 1.

Referring now to FIG. 3, the external features of the stimulation leads 12 and the IPG 14 will be briefly described. Each of the stimulation leads 12 has eight electrodes 26 (respectively labeled E1-E8, E9-E16, and E17-E24). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

Figure 4:
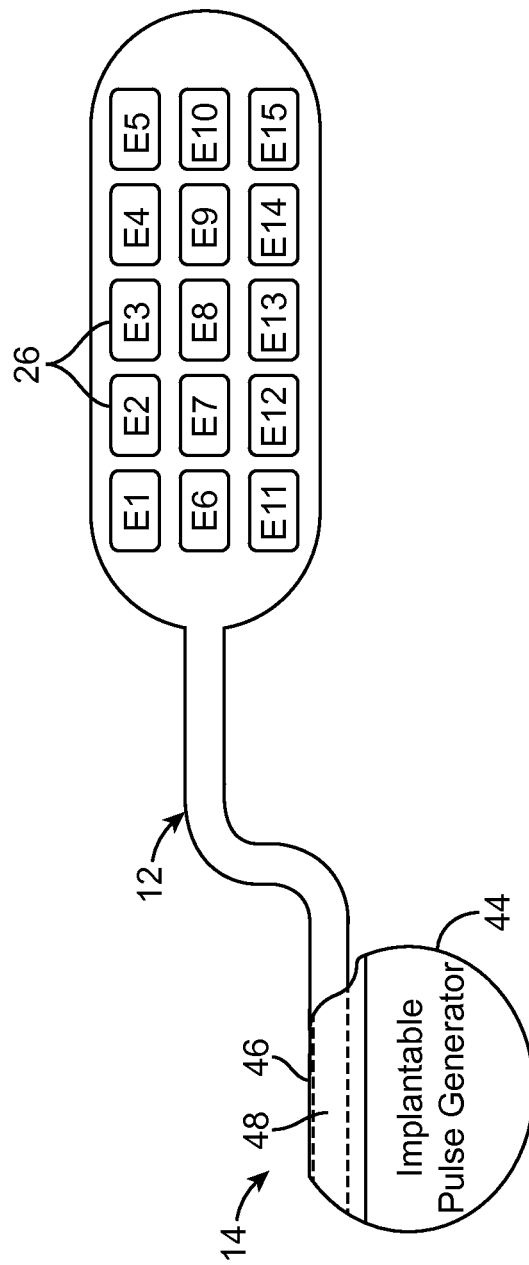
FIG. 4 is a plan view of an implantable pulse generator (IPG) and a surgical paddle lead used in the SCS system of FIG. 2.

Alternatively, as illustrated in FIG. 4, the stimulation lead 12 takes the form of a surgical paddle lead on which electrodes 26 are arranged in a two-dimensional array in three columns (respectively labeled E1-E5, E6-E10, and E11-E15) along the axis of the stimulation lead 12. In the illustrated embodiment, five rows of electrodes 26 are provided, although any number of rows of electrodes can be used. Each row of the electrodes 26 is arranged in a line transversely to the axis of the lead 12. The actual number of leads and electrodes will, of course, vary according to the intended application. Further details regarding the construction and method of manufacture of surgical paddle leads are disclosed in U.S. patent application Ser. No. 11/319,291, entitled "Stimulator Leads and Methods for Lead Fabrication," the disclosure of which is expressly incorporated herein by reference.

In each of the embodiments illustrated in FIGS. 3 and 4, the IPG 14 comprises an outer case 44 for housing the electronic and other components (described in further detail below). The outer case 44 is composed of an electrically conductive, biocompatible material, such as titanium, and forms a hermetically sealed compartment wherein the internal electronics are protected from the body tissue and fluids. In some cases, the outer case 44 may serve as an electrode. The IPG 14 further comprises a connector 46 to which the proximal ends of the stimulation leads 12 mate in a manner that electrically couples the electrodes 26 to the internal electronics (described in further detail below) within the outer case 44. To this end, the connector 46 includes one or more ports (three ports 48 or three percutaneous leads or one port for the surgical paddle lead) for receiving the proximal end(s) of the stimulation lead(s) 12. In the case where the lead extensions 24 are used, the port(s) 48 may instead receive the proximal ends of such lead extensions 24.

The IPG 14 includes pulse generation circuitry that provides electrical conditioning and stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

Electrical stimulation will occur between two (or more) activated electrodes, one of which may be the IPG case 44. Simulation energy may be transmitted to the tissue in a monopolar or multipolar (e.g., bipolar, tripolar, etc.) fashion. Monopolar stimulation occurs when a selected one of the lead electrodes 26 is activated along with the case 44 of the IPG 14, so that stimulation energy is transmitted between the selected electrode 26 and the case 44. Bipolar stimulation occurs when two of the lead electrodes 26 are activated as anode and cathode, so that stimulation energy is transmitted between the selected electrodes 26. For example, an electrode on one lead 12 may be activated as an anode at the same time that an electrode on the same lead or another lead 12 is activated as a cathode. Tripolar stimulation occurs when three of 15 the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

Figure 5:
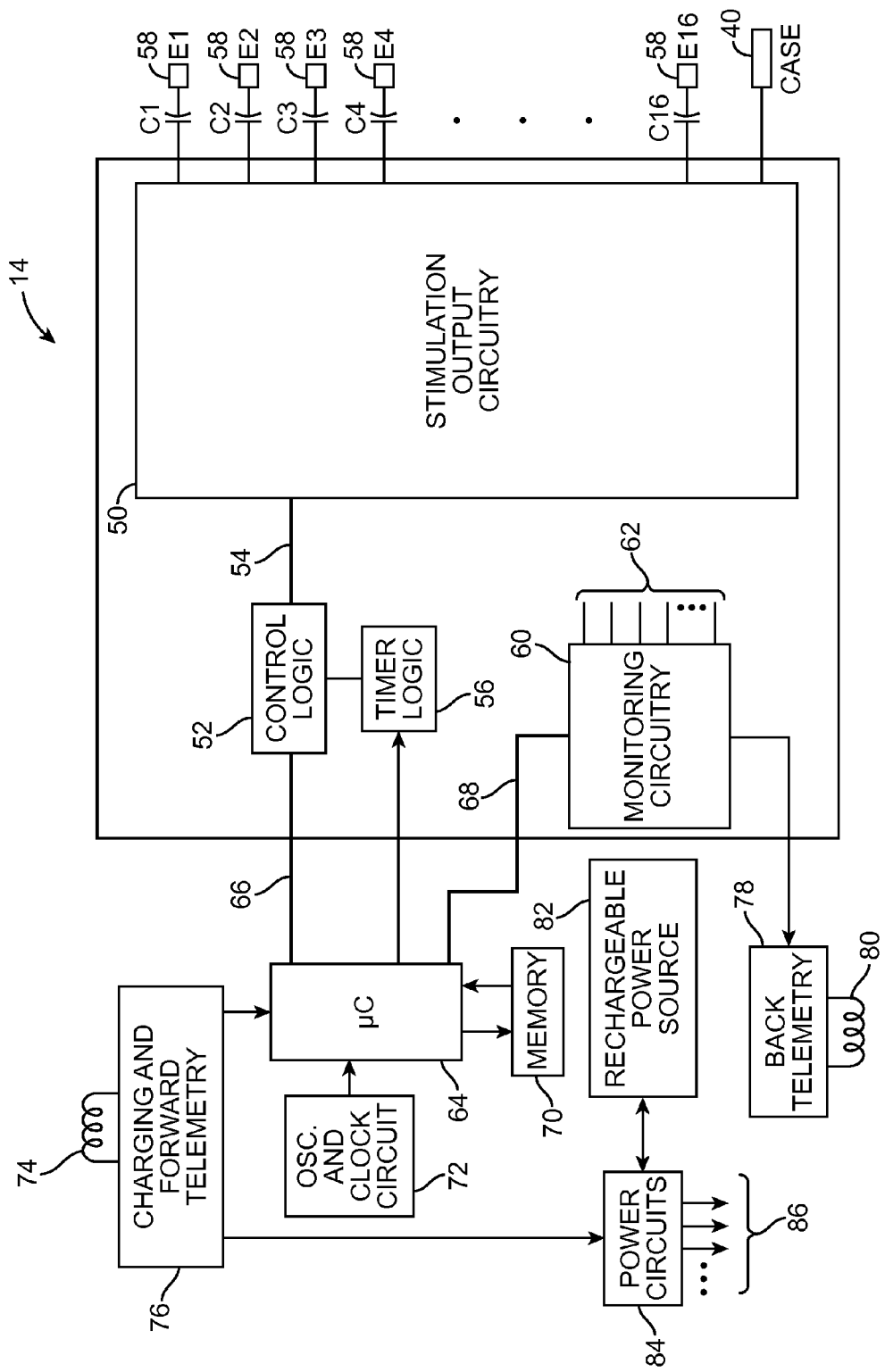
FIG. 5 is a block diagram of the internal components of the IPG of FIG. 5.

Turning next to FIG. 5, the main internal components of the IPG 14 will now be described. The IPG 14 includes stimulation output circuitry 50 configured for generating electrical stimulation energy in accordance with a defined pulsed waveform having a specified pulse amplitude, pulse rate, pulse width, pulse shape, and burst rate under control of control logic 52 over data bus 54. Control of the pulse rate and pulse width of the electrical waveform is facilitated by timer logic circuitry 56, which may have a suitable resolution, e.g., 10 μs. The stimulation energy generated by the stimulation output circuitry 50 is output via capacitors C1-Cn to electrical terminals 58 corresponding to the electrodes 26. In the illustrated embodiment, the stimulation output circuitry 50 may either comprise independently controlled current sources for providing stimulation pulses of a specified and known amperage to or from the electrodes 26, or independently controlled voltage sources for providing stimulation pulses of a specified and known voltage at the electrodes 26. As will be described in further detail below, the stimulation output circuitry 50 further includes charge recovery circuitry to provide charge balancing of the electrodes and recovery of charge from the tissue.

The IPG 14 further comprises monitoring circuitry 60 for monitoring the status of various nodes or other points 62 throughout the IPG 14, e.g., power supply voltages, temperature, battery voltage, and the like. The monitoring circuitry 60 is also configured for measuring electrical parameter data (e.g., electrode impedance and/or electrode field potential). The IPG 14 further comprises processing circuitry in the form of a microcontroller (μC) 64 that controls the control logic 52 over data bus 66, and obtains status data from the monitoring circuitry 60 via data bus 68. The IPG 14 additionally controls the timer logic 56. The IPG 14 further comprises memory 70 and oscillator and clock circuit 72 coupled to the microcontroller 64. The microcontroller 64, in combination with the memory 70 and oscillator and clock circuit 72, thus comprise a microprocessor system that carries out a program function in accordance with a suitable program stored in the memory 70. Alternatively, for some applications, the function provided by the microprocessor system may be carried out by a suitable state machine.

Thus, the microcontroller 64 generates the necessary control and status signals, which allow the microcontroller 64 to control the operation of the IPG 14 in accordance with a selected operating program and stimulation parameters. In controlling the operation of the IPG 14, the microcontroller 64 is able to individually generate stimulus pulses at the electrodes 26 using the stimulation output circuitry 50, in combination with the control logic 52 and timer logic 56, thereby allowing each electrode 26 to be paired or grouped with other electrodes 26, including the monopolar case electrode, to control the polarity, amplitude, rate, pulse width and channel through which the current stimulus pulses are provided.

The IPG 14 further comprises an alternating current (AC) receiving coil 74 for receiving programming data (e.g., the operating program and/or stimulation parameters) from the RC 16 and/or CP 18 in an appropriate modulated carrier signal, and charging and forward telemetry circuitry 76 for demodulating the carrier signal it receives through the AC receiving coil 74 to recover the programming data, which programming data is then stored within the memory 70, or within other memory elements (not shown) distributed throughout the IPG 14.

The IPG 14 further comprises back telemetry circuitry 78 and an alternating current (AC) transmission coil 80 for sending informational data sensed through the monitoring circuitry 60 to the RC 16 and/or CP 18. The back telemetry features of the IPG 14 also allow its status to be checked. For example, when the RC 16 and/or CP 18 initiates a programming session with the IPG 14, the capacity of the battery is telemetered, so that the RC 16 and/or CP 18 can calculate the estimated time to recharge. Any changes made to the current stimulus parameters are confirmed through back telemetry, thereby assuring that such changes have been correctly received and implemented within the implant system. Moreover, upon interrogation by the RC 16 and/or CP 18, all programmable settings stored within the IPG 14 may be uploaded to the RC 16 and/or CP 18.

The IPG 14 further comprises a rechargeable power source 82 and power circuits 84 for providing the operating power to the IPG 14. The rechargeable power source 82 may, e.g., comprise a lithium-ion or lithium-ion polymer battery. The rechargeable battery 82 provides an unregulated voltage to the power circuits 84 (e.g., 3V). The power circuits 84, in turn, generate the various voltages 86, some of which are regulated and some of which are not, as needed by the various circuits located within the IPG 14. As will be described in further detail below, the power circuits 84 include a high voltage generation (HVG) circuit that converts the battery voltage to a higher voltage under control of the microcontroller 64 in order to prevent electrical current induced by strong magnetic fields, such as those generated by magnetic resonance image (MRI) scanners, from creating a loop within the charge recovery circuit that could cause inadvertent stimulation of the patient.

The rechargeable power source 82 is recharged using rectified AC power (or DC power converted from AC power through other means, e.g., efficient AC-to-DC converter circuits, also known as "inverter circuits") received by the AC receiving coil 74. To recharge the power source 82, the external charger 22 (shown in FIG. 1), which generates the AC magnetic field, is placed against, or otherwise adjacent, to the patient's skin over the implanted IPG 14. The AC magnetic field emitted by the external charger induces AC currents in the AC receiving coil 74. The charging and forward telemetry circuitry 76 rectifies the AC current to produce DC current, which is used to charge the power source 82. While the AC receiving coil 74 is described as being used for both wirelessly receiving communications (e.g., programming and control data) and charging energy from the external device, it should be appreciated that the AC receiving coil 74 can be arranged as a dedicated charging coil, while another coil, such as coil 80, can be used for bi-directional telemetry.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the system 10 may alternatively utilize an implantable receiver-stimulator (not shown) connected to leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 6:
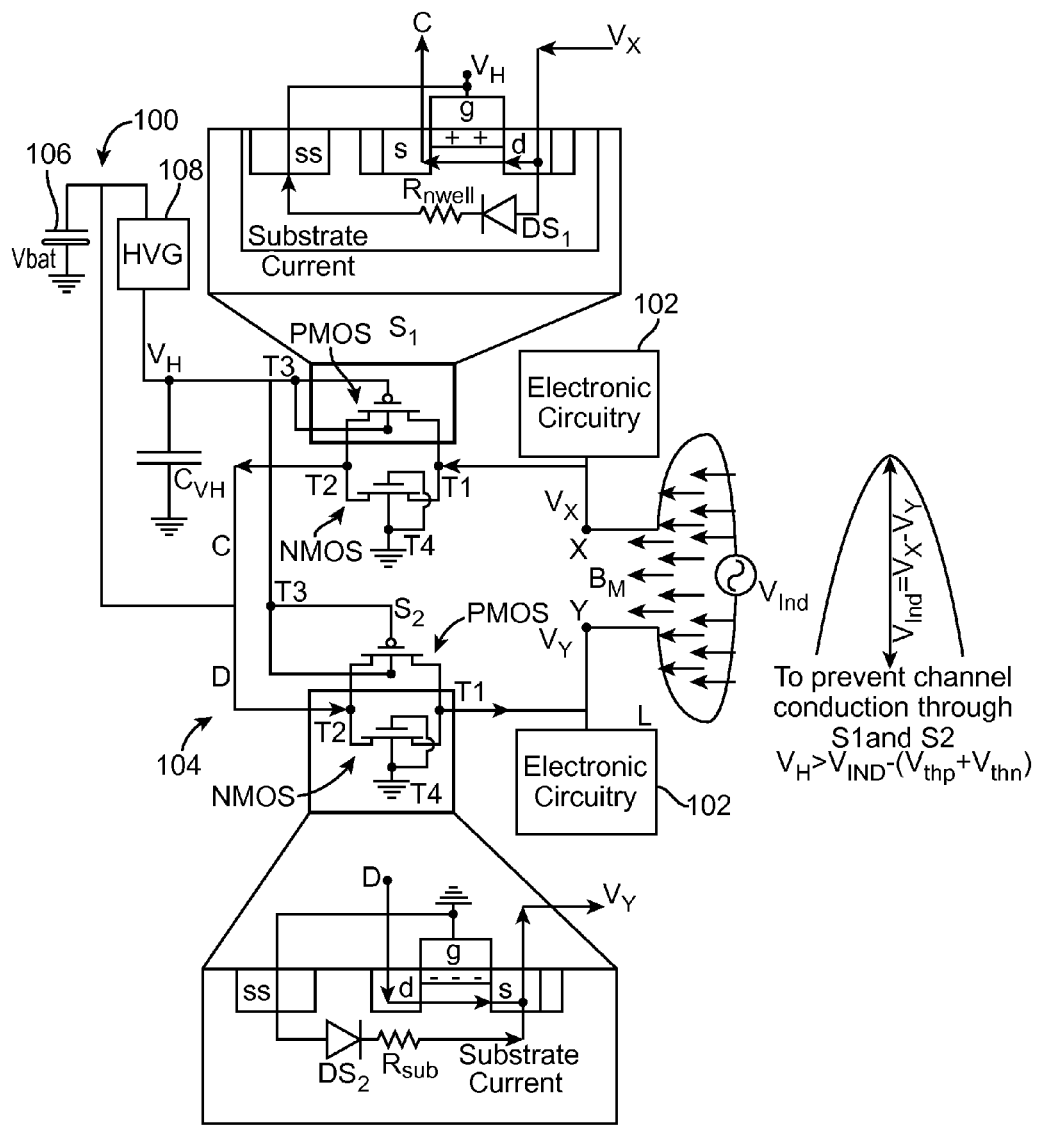
FIG. 6 is a block diagram illustrating the pertinent components of the stimulation output circuitry contained in the IPG of FIG. 5.

Referring now to FIG. 6, the stimulation output circuitry 50 comprises a variable power supply 100 used to regulated voltage to the remaining components of the stimulation output circuitry 50, an active stimulation circuit 102 configured for conveying a train of stimulation pulses when the IPG 14 is in an active stimulation state, and a passive charge recovery circuit 104 configured for recovering charge when the IPG 14 is in the active stimulation state. The variable power supply 100 includes a battery 106, which outputs a fixed voltage $V_{bat}$ (e.g., 3 volts), and a high voltage generation (HVG) circuit 108 capable of converting the fixed voltage of the battery 106 to a higher voltage $V_H$ (e.g., 18 volts). Thus, the variable power supply 100 may output a relatively low voltage (e.g., less than 5 volts) by turning off the HVG circuit 108, and a relatively high voltage (e.g., greater than 10 volts) by turning on the HVG circuit 108 to pump the voltage to $V_H$. For the purposes of this specification, a relatively low voltage and a relatively high voltage are relative to each other and simply means that between two voltages, the lower voltage can be considered the relatively low voltage, while the higher voltage can be considered the relatively high voltage.

The passive charge recovery circuit 104 includes a plurality of switching devices respectively coupled to the plurality of electrical terminals 58. For purposes of brevity, only two of the switching devices $S_1$, $S_2$ are illustrated to demonstrate how charge may be recovered from tissue by shorting two of the active electrical terminals (x and y) together through the switching devices $S_1$, $S_2$ (one being used to conduct anodic electrical current during the active stimulation state, and one being used to conduct cathodic electrical current during the active stimulation state). The switching devices $S_1$, $S_2$ are shorted together respectively at points C and D to AC ground, and in particular, the output to the battery 108.

During normal operation, the switching devices $S_1$, $S_2$ are open during the duration of each stimulation pulse, and closed between the conveyance of the stimulation pulses. When both the switching devices $S_1$, $S_2$ are open, no portion of the stimulation pulses generated by the active stimulation circuitry 104 are conveyed back through the switching devices $S_1$, $S_2$, so that all of the stimulation energy is conveyed to the respective electrodes 26 via the electrical terminals 58. When both the switching devices $S_1$, $S_2$ are closed, the passive charge recovery mode is activated for charge balancing on the electrodes; that is, any charge on the electrodes 26 is conveyed through the closed switching devices $S_1$, $S_2$ to discharge the tissue, and in particular, the electrical current is passively conveyed from the anodic electrode to the cathodic electrode via the switching devices $S_1$, $S_2$ to discharge the tissue.

Coincidentally, the switches $S_1$, $S_2$ contribute to the problem of creating an electrical current loop within the passive charge recovery circuit 104 in response to a strong gradient magnetic field generated by an MRI scanner even when the IPG 14 is in an inactive stimulation state (i.e., no train of stimulation pulses is actively being conveyed to the patient by the active stimulation circuit 102), which may result in inadvertent stimulation of the patient. Significant to the present inventions, the variable power supply 100 can, when the IPG 14 is in the inactive stimulation output (i.e., it is not currently conveying a series of stimulation pulses), selectively output different voltage levels as discussed above, and in particular, the relatively low voltage level during non-MRI conditions, and a relatively high voltage level during MRI conditions, such that electrical energy induced on electrical terminals 58 by an external energy (e.g., a gradient magnetic field generated by an MRI scanner) is preventing from being conveyed through the passive charge recovery circuit 104 and out to the electrodes 26, which may otherwise cause inadvertent and undesirable stimulation of the patient, as will be described in further detail below. In the illustrated embodiment, when the IPG 14 is in the active stimulation state (i.e., it is currently conveying a series of stimulation pulses), the variable power supply 100 outputs the same relatively high voltage level that is output during MRI conditions. However, the voltages output from the variable power supply 100 can be different when the IPG 14 is in the inactive stimulation state during MRI conditions and when the IPG 14 is in the active stimulation state.

Each of the switching devices $S_1$, $S_2$ includes a first through terminal $T_1$ coupled to one of the electrical terminals x, y, a second through terminal $T_2$ that are shorted to each other through points C, D, and two control terminals $T_3$, $T_4$, both coupled between either the output of the HVG circuit 100 or ground. Although for purposes of illustration only, the control terminals $T_3$ of the switching devices $S_1$, $S_2$ are shown hardwired to the output of the variable output supply 100 and the control terminals $T_4$ of the switching devices $S_1$, $S_2$ are shown hardwired to ground, control logic (not shown) may be provided to allow the output of the variable output supply 100 or ground to be selectively coupled to the control terminals $T_3$ of the switching devices $S_1$, $S_2$, and the output of the variable output supply 100 or ground to be selectively coupled to the control terminals $T_4$ of the switching devices $S_1$, $S_2$. As will be discussed in further detail below, the alternate switching of the variable output supply 100 and ground to the control terminals $T_3$, $T_4$ of the switching devices $S_1$, $S_2$ allows the switching devices $S_1$, $S_2$ to be selectively opened and closed. The HVG circuit 100 outputs a voltage $V_H$ that is stored in capacitor $C_{VH}$.

In the illustrated embodiment, the two switching devices $S_1$, $S_2$ take the form of solid-state switches, and in particular, complementary Metal-Oxide Semiconductor (CMOS) transmission-gate switches. That is, each of the switching devices $S_1$, $S_2$ includes a P-channel metal-oxide semiconductor (PMOS) transistor and an N-channel metal-oxide semiconductor (NMOS) transistor, so that when closed during the active stimulation state, both switching devices $S_1$, $S_2$ can conduct electrical current in both directions to take into the account both cases where the electrical terminals x, y (and thus the electrodes coupled to them) are respectively anodic and cathodic or the electrical terminals x, y (and thus the electrode coupled to them) are respectively cathodic and anodic.

As shown, the first and second through terminals $T_1$, $T_2$ of the switching device $S_1$ are respectively coupled to the drain terminal d and source terminal s of the PMOS transistor, and the first and second through terminals $T_1$, $T_2$ of the switching device $S_2$ are respectively coupled to the source terminal s and drain terminal d of the NMOS transistor. Similarly, the first and second through terminals $T_1$, $T_2$ of the switching device $S_1$ are respectively coupled to the source terminal s and drain terminal d of the NMOS transistor, and the first and second through terminals $T_1$, $T_2$ of the switching device $S_2$ are respectively coupled to the drain terminal d and source terminal s of the PMOS transistor. The control terminal $T_3$ of each of the switching devices $S_1$, $S_2$ is coupled to the gate terminal g and substrate terminal ss of the respective PMOS transistors, and the control terminal $T_4$ of each of the switching devices $S_1$, $S_2$ is coupled to the gate terminal g and substrate terminal ss of the respective NMOS transistors.

During normal operation (i.e., when no external magnetic fields are present), the switching devices $S_1$, $S_2$ are opened during the conveyance of each stimulation pulse, and are closed after the conveyance of each stimulation pulse. In this particular case, the microcontroller 62 opens the switching devices $S_1$, $S_2$ by prompting the HVG circuit 106 of the variable power supply 100 to pump the control terminals $T_3$ (i.e., the terminals coupled to the PMOS transistors) with a relatively high voltage (e.g., 18 volts), and grounding the control terminals $T_4$ (i.e., the terminals coupled to the NMOS transistors). In contrast, the microcontroller 62 closes the switching devices $S_1$, $S_2$ by grounding the control terminals T$_3$ (i.e., the terminals coupled to the PMOS transistors) and prompting the HVG circuit 106 of the variable power supply 100 to pump the control terminals T$_4$ (i.e., the terminals coupled to the NMOS transistors) with a relatively high voltage (e.g., 18 volts).

As briefly discussed above, during an MRI scan, electrical current may be conveyed through the switching devices S$_1$, S$_2$, thereby inadvertently stimulating the patient. In order to fully understand the technique used to prevent conduction of induced electrical current through the switching devices S$_1$, S$_2$, it is important to explain the circumstances under which the switching devices S1, S2 turn on.

Consider the case when a stimulation lead L forms a loop exposed to a changing magnetic field, B$_M$, which induces a voltage V$_{ind}$ (i.e., V$_x$-V$_y$) on the stimulation lead L proportional to its rate of change, dB$_M$/dt. If the capacitor C$_{VH}$ is charged to a voltage V$_H$ output by the HVG circuit 100, such that the voltage V$_x$ on the electrical terminal x exceeds the voltage V$_H$ by more than the forward bias voltage of the substrate diode DS$_1$ in the PMOS transistor of the switching device S$_1$, the substrate diode DS$_1$ turns on, thereby creating a substrate current. When the substrate current flows, due to the finite Nwell resistance R$_{Nwell}$, the area under the control gate g is no longer at V$_H$, thereby becoming inverted. The PMOS transistor in the switching device S$_1$ turns on when the voltage V$_x$ exceeds the voltage V$_H$ by its threshold voltage |V$_{thp}$|. A similar phenomenon occurs with the NMOS transistor. That is, if the voltage V$_y$ on the electrical terminal y is below ground, the substrate diode DS$_2$ turns on, thereby creating a substrate current. When the substrate current flows, due to the finite Nwell resistance R$_{Nwell}$, the area under the control gate g is no longer at ground, thereby becoming inverted. The NMOS transistor in the switching device S$_2$ turns on when the voltage V$_y$ is less than ground by its threshold voltage |V$_{thn}$|.

When the voltage V$_H$ is greater than [V$_{thn}$|+|V$_{thp}$|] (typically 1-1.5V depending on the process technology), but below the induced voltage V$_{ind}$, there is channel conduction through the PMOS transistor of the switching device S$_1$ and the NMOS transistor of the switching device S$_2$. When the polarity of the induced voltage V$_{ind}$ is reversed, the situation is symmetrically identical; that is, the PMOS transistor in the switching device S2 turns on when the voltage V$_y$ exceeds the voltage V$_H$ by its threshold voltage |V$_{thp}$|, and the NMOS transistor in the switching device S$_1$ turns on when the voltage V$_x$ is less than ground by its threshold voltage |V$_{thn}$|. Thus, when the voltage V$_H$ is greater than [V$_{thn}$|+|V$_{thp}$|] (typically 1-1.5V depending on the process technology), but below the induced voltage V$_{ind}$, there is channel conduction through the PMOS transistor of the switching device S$_2$ and the NMOS transistor of the switching device S$_1$. Thus, even if the switching devices S$_1$, S$_2$ are open, it is possible for induced voltage V$_{ind}$ to cause electrical current to flow through the switching devices S$_1$, S$_2$ (turning the switching devices S$_1$, S$_2$ ON) thus closing the loop between the electrodes.

Normally, the microcontroller 64 prompts the variable power supply 100 to output a relatively low voltage when the IPG 14 is in the inactive stimulation state. In the illustrated embodiment, this is accomplished by turning off the HVG circuit 106 of the variable power supply 100, thereby effectively passing through the battery voltage Vbat to the control terminals T3 (i.e., the terminals coupled to the PMOS transistors). To prevent channel conduction through both of the switching devices S$_1$, S$_2$ when the patient is subjected to an MRI scan, the microcontroller 64 prompts the HVG circuit 106 of the variable power supply 100 to pump the control terminals T$_3$ (i.e., the terminals coupled to the PMOS transistors) with a relatively high voltage (e.g., 18 volts). Preferably, the microcontroller 64 prompts the HVG circuit 106 to pump the control terminals T$_3$ of the switching devices S$_1$, S$_2$ with the relatively high voltage in response to an external signal received by the forward telemetry circuitry 76 (shown in FIG. 5) from the RC 16 or CP 18, or alternatively a sensor (not shown) specially designed for sensing a strong magnetic field (which will serve as the external signal) generated by an MRI scanner, as distinguished from a relatively weak magnetic gradient field produced by a magnet designed to activate a reed switch to turn off the IPG 14.

Figure 7:
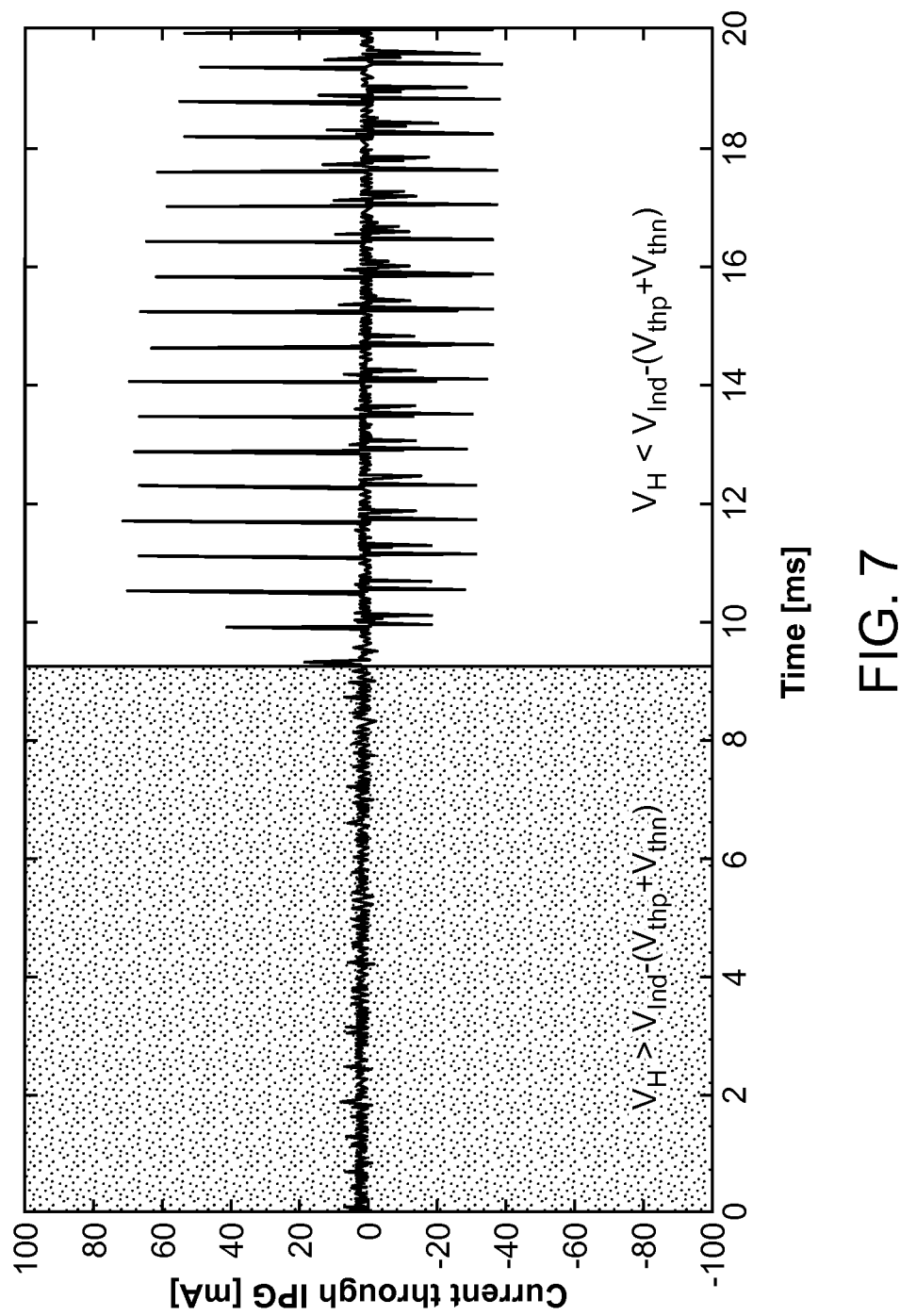
FIG. 7 is a diagram illustrating the induced electrical current in the passive charge recovery circuit of a commercial embodiment of an IPG when subjected to magnetic energy generated by a magnetic resonance image (MRI) scanner.

Referring to FIG. 7, an experiment was conducted measuring the electrical current flowing through the passive recovery switch circuit of a commercial embodiment of an IPG versus times when exposed to a magnetic gradient field generated by a conventional MRI gradient coil apparatus. When the passive recovery switches of the commercial IPG 14 were pumped with a voltage greater than the voltage induced by the MRI apparatus minus the threshold voltages of the recovery switches (V$_H$>V$_{ind}$−(V$_{thp}$+V$_{thn}$)), the electrical current induced at the electrical terminals of the IPG 14 were blocked as shown by the left side of the diagram illustrated in FIG. 7. However, when the passive recovery switches of the commercial IPG 14 were pumped with a voltage less than the voltage induced by the MRI apparatus minus the threshold voltages of the recovery switches (V$_H$>V$_{ind}$−(V$_{thp}$+V$_{thn}$)), the electrical current induced at the electrical terminals of the IPG 14 were not blocked as shown by the right side of the diagram illustrated in FIG. 7.

As briefly discussed above, a conventional IPG contains a magnetic field sensing mechanism, such as a Reed Switch or a Hall Effect sensor that prompts deactivation of the IPG in the presence of an external magnetic field, typically referred to as a "Reset Mode" or "Magnet Mode." The IPG 14 operates in a similar manner; however, in order to enable the voltage of the variable power supply 100 to be increased to prevent the conduction of induced electrical current through the passive charge recovery circuit 104, in response to an external programming signal generated by the RC 16 or CP 18, and received by the forward telemetry circuitry 76 (e.g., the patient or clinician can send such a programming signal in anticipation of an MRI), the microcontroller 62 prevents the IPG 16 from being deactivated.

For example, the microcontroller 76 may prevent the IPG 14 from being deactivated by disabling the magnetic sensing mechanism. In one example, as shown in FIG. 8, a prior art embodiment includes a reed switch 200 coupled between either the battery voltage or ground and a reset management component 202, which, depending on the logic, may output an active low or an active high to reset the IPG. As shown in FIG. 9, the microcontroller 62 in the IPG 14 operates an enabling/disabling switch 204 that connects either the battery voltage or ground to the reed switch 200 to alternately disable the reed switch 200. For example, in the case where the reed switch 200 would normally be hardwired to the battery voltage, the microcontroller 62 will operate the enabling/disabling switch 204 to couple the reed switch 200 to the battery voltage to enable the reed switch 200 and couple the reed switch 200 to ground to disable the reed switch 200. In the alternative case where the reed switch 200 would normally be hardwired to ground, the microcontroller 62 will operate the enabling/disabling switch 204 to couple the reed switch 200 to ground to enable the reed switch 200 and couple the reed switch 200 to the battery voltage to disable the reed switch 200.

Figure 10:
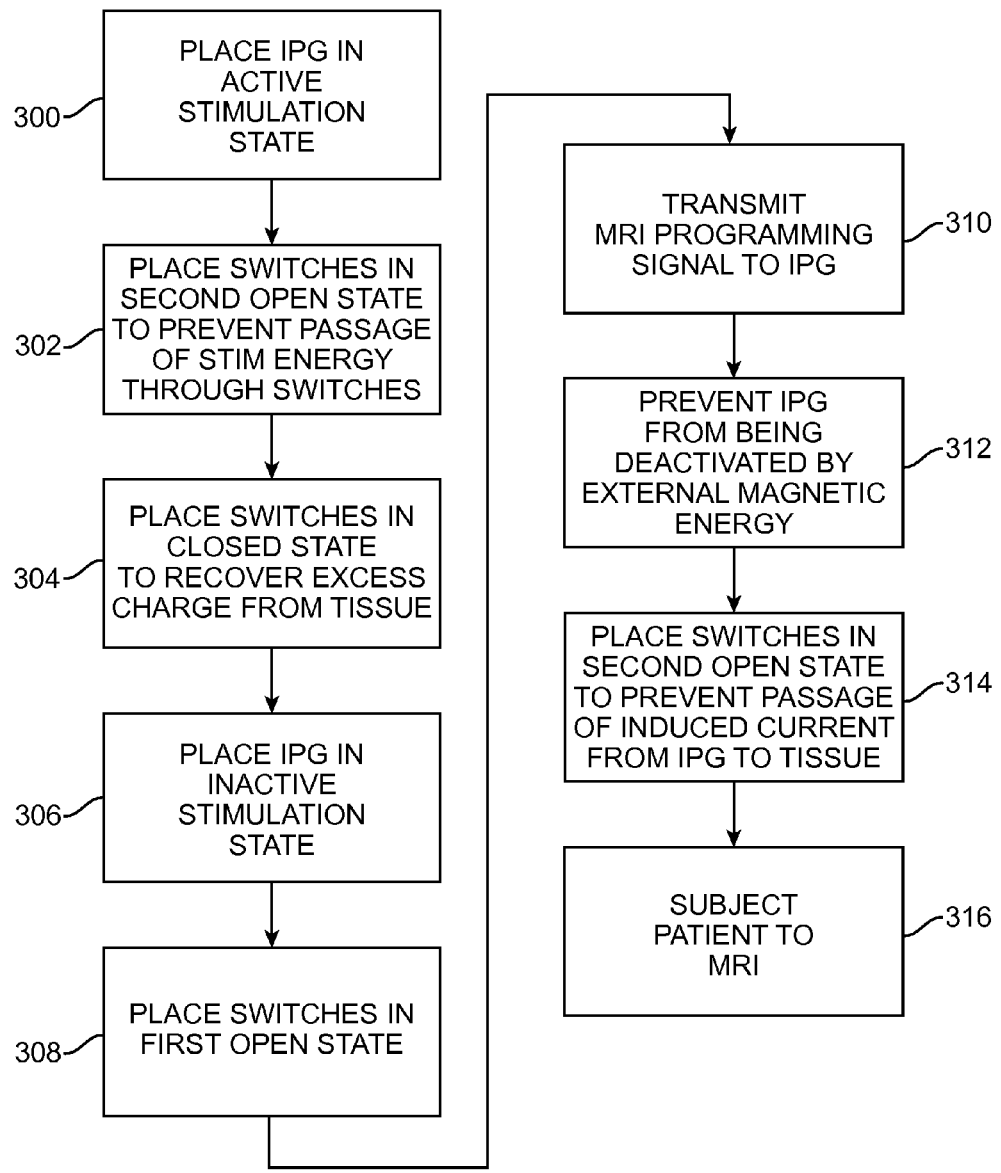
FIG. 10 is a flow diagram illustrating a technique used by the neurostimulation system of FIG. 1 to deliver stimulation energy to tissue, recover charge from the tissue using the passive charge recovery circuit of FIG. 6, and to prevent the induction of electrical current within the passive charge recovery circuit when subjected to an MRI.

Having described the structure and function of the SCS system 10, one technique for operating the system 10 to prevent induced electrical current from being conducted through the passive charge recovery circuit 104 will now be described with reference to FIG. 10. The technique is described, such that the system 10 is operated conventionally to stimulate the patient, thereby providing therapy (steps 300-304), and then configured to protect the patient and/or electronics during an MRI scan (steps 306-316).

First, the IPG 14 may be operated in a stimulation mode (i.e., the IPG 14 is placed in an active stimulation state), during which a train of stimulation pulses are conveyed from the active stimulation circuit 102 of the IPG 14 to the stimulation leads 12 to provide neurostimulation therapy to the patient, and in the illustrated case, to treat chronic pain (step 300). During the conveyance of each stimulation pulse, the microcontroller 62 prompts the variable power supply 100 to apply a relatively high voltage to the control gates of the PMOS transistors of the passive charge recovery circuit 104, and grounding the control gates of the NMOS transistors of the passive charge recovery circuit 104, thereby opening the PMOS and NMOS switches to place the switching devices in a second open state and preventing any stimulation energy from entering the charge recovery circuit 104 (step 302). When no stimulation pulse is presently being conveyed (i.e., between the stimulation pulses), the microcontroller 62 prompts the variable power supply 100 to apply a relatively high voltage to the control gates of the NMOS transistors of the passive charge recovery circuit 104, and grounding the control gates of the PMOS transistors of the passive charge recovery circuit 104, thereby closing the PMOS and NMOS switches to place the switching devices in a closed state and recovering any charge in the tissue previously caused by the stimulation pulses (step 304).

The IPG 14 may be operated in a standby mode (i.e., the IPG 14 is placed in an inactive stimulation state), during which no stimulation pulses are conveyed from the active stimulation circuit 102 of the IPG 14 to the stimulation leads 12 (step 306). During this time, the microcontroller 62 prompts the variable power supply 100 to apply a relatively low voltage to the control gates of the PMOS transistors of the passive charge recovery circuit 104, and grounding the control gates of the NMOS transistors of the passive charge recovery circuit 104, thereby opening the PMOS and NMOS switches to place the switching devices in a first open state (step 308). Because the application of the voltage by the variable power supply 100 is relatively low, power is conserved.

In anticipation of the patient being subject to high gradient magnetic fields, such as those created by an MRI scanner, a programming signal can be transmitted to the IPG 14 (step 310). In response, the microcontroller 62 prevents the IPG 14 from being deactivated by the magnetic energy by disabling the reed switch 200 (step 312) and prompts the variable power supply 100 to apply the relatively high voltage to the control gates of the PMOS transistors of the passive charge recovery circuit 104, and grounding the control gates of the NMOS transistors of the passive charge recovery circuit 104, thereby opening the PMOS and NMOS switches to place the switching devices in a second open state (step 314). The patient is then subjected to an MRI, thereby creating a gradient magnetic field that induces a voltage on the electrical terminals 58 of the IPG 14 via the stimulation leads 12 (step 316). Although this induced voltage may otherwise cause an electrical current to be conducted through the passive charge recovery circuit 104 when the relatively low voltage is applied to the control gates of the PMOS transistors, the relatively high voltage that is applied to the control gates of the PMOS transistors prevents the electrical current from being conducted through the passive charge recovery circuit 104.

Although the external energy that potentially induces electrical current in the passive charge recovery circuit 104 has been described as being a gradient magnetic field generated by an MRI scanner, it should be appreciated that other external energy, such as the radio frequency (RF) electric fields generated by an MRI scanner or other source can potentially induce electrical current in the passive charge recovery circuit 104, which can be prevented in the same manner described above. Furthermore, although the switching devices through which electrical current could be potentially induced have been described as passive charge recovery switches, it should be appreciated that the present inventions can be utilized to prevent the induction of electrical current within other switches within the IPG 14, e.g., switches between the stimulation sources and the electrical terminals.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neurostimulation device capable of being placed between a stimulation mode for delivery of a series of stimulation pulses and a standby mode, comprising:
    a plurality of electrical terminals configured for being respectively coupled to a plurality of stimulation electrodes;
    a first solid-state switching device coupled to a first one of the electrical terminals, wherein the first solid-state switching device has a closed state in which current can flow through the first solid-state switching device and first and second open states in which flow of current through the first solid-state switching device is prevented if the current is below a threshold;
    a variable power source coupled to the first switching device; and
    a controller configured for placing the neurostimulation device in the stimulation mode for delivering the series of stimulation pulses and placing the neurostimulation device in the standby mode when not delivering the series of stimulation pulses, wherein the controller is further configured for, when the neurostimulation device is in the standby mode, prompting the variable power source to selectively output a relatively low voltage to place the first switching device into a first open state and a relatively high voltage to place the first switching device into a second open state and, when the neurostimulation device is in the stimulation mode for delivering the series of stimulation pulses, prompting the variable power source to output the relatively high voltage to place the first switching device into the second open state during conveyance of each of the pulses in the series of stimulation pulses and into the closed state between the pulses of the series.

2. The neurostimulation device of claim 1, further comprising a second solid-state switching device coupled to a second one of the electrical terminals, wherein the second solid-state switching device has a closed state in which current can flow through the second solid-state switching device and first and second open states in which flow of current through the second solid-state switching device is prevented if the current is below a threshold,
wherein the first and second switching devices are shorted to each other, wherein the variable power source is coupled to the second switching device, and the controller is configured for, when the neurostimulation device is in the standby mode, prompting the variable power source to selectively output the relatively low voltage to place the second switching device into the first open state and the relatively high voltage to place the second switching device into the second open state and, when the neurostimulation device is in the stimulation mode for delivering the series of stimulation pulses, prompting the variable power source to output the relatively high voltage to place the second switching device into the second open state during conveyance of each of the pulses in the series of stimulation pulses and into the closed state between the pulses of the series of stimulation pulses.

3. The neurostimulation device of claim 2, wherein each of the first and second switching devices comprises two complementary transmission gate switches.

4. The neurostimulation device of claim 3, wherein the two complementary transmission gate switches comprises an N-channel metal-oxide semiconductor (NMOS) transistor and a P-channel metal-oxide semiconductor (PMOS).

5. The neurostimulation device of claim 2, further comprising at least one stimulation source, wherein the controller is configured for prompting the at least one stimulation source to convey the series of stimulation pulses between the first and second electrical terminals when the neurostimulation device is in the stimulation mode, and for prompting the variable power source to ground the first switch after the conveyance of each of the pulses to place the first switching device into a closed state.

6. The neurostimulation device of claim 2, further comprising a passive charge recovery circuit comprising the first and second switching devices and configured and arranged, when coupled to the plurality of stimulation electrodes through the plurality of electrical terminals, to permit charge balancing between the plurality of stimulation electrodes when the first and second switching devices are both in the closed state.

7. The neurostimulation device of claim 1, wherein the relatively low voltage is less than five volts, and the relatively high voltage is greater than ten volts.

8. The neurostimulation device of claim 1, further comprising telemetry circuitry configured for receiving a signal external to the neurostimulation device, wherein the controller is configured for prompting the variable power source to output the relatively high voltage in response to the external signal.

9. The neurostimulation device of claim 8, further comprising a sensing mechanism configured for deactivating the neurostimulation device in the presence of an external magnetic field, wherein the controller, in response to the external signal, is configured for preventing the neurostimulation device from being deactivated.

10. The neurostimulation device of claim 9, wherein the controller is configured for preventing the neurostimulation device from being deactivated by disabling the sensing mechanism.

11. The neurostimulation device of claim 1, wherein the variable power supply comprises a battery configured for outputting the relatively low voltage, and a high voltage circuit coupled to the battery and configured for increasing an output voltage of the battery for outputting the relatively high voltage.

12. The neurostimulation device of claim 11, wherein the controller is configured for turning off the high voltage circuit to pass the relative low voltage from the battery to the first switching device, and for turning on the high voltage circuit to output the relatively high voltage from the high voltage circuit to the first switching device.

13. The neurostimulation device of claim 1, wherein the first switching device has a control terminal, and the controller is configured for, when the neurostimulation device is in the standby mode, prompting the variable power source to selectively output the relatively low voltage to the control terminal of the first switching device and the relatively high voltage to the control terminal of the first switching device.

14. A method of preventing induced electrical current in the neurostimulation device of claim 1, the neurostimulation device being associated with a patient exposed to external energy, the method comprising:
placing the neurostimulation device in the standby mode;
applying the relatively low voltage to the first switching device when the neurostimulation device is in the standby mode, thereby placing the first switching device in the first open state;
applying the relatively high voltage to the second switching device when the neurostimulation device is in the standby mode, thereby placing the first switching device in the second open state; and
applying the external energy to the patient, thereby inducing a voltage on the first electrical terminal, wherein the induced voltage is at a level that is prevented from conducting current through the first switching device when in the second open state that would otherwise be conducted through the first switching device when in the first open state.

15. The method of claim 14, wherein the external energy is magnetic energy.

16. The method of claim 14, wherein the magnetic energy is a gradient magnetic field generated by a magnetic resonance imaging (MRI) scanner.

17. The method of claim 14, wherein a first stimulating electrode is carried by a stimulation lead coupled to the neurostimulation device.

18. The method of claim 14, wherein the neurostimulation device includes a second solid-state switching device coupled to a second stimulation electrode via a second electrical terminal, the method further comprising:
applying the relatively low voltage to the second switching device when the neurostimulation device is in the standby mode, thereby placing the second switching device in a first open state;
applying the relatively high voltage to the second switching device when the neurostimulation device is in the standby mode, thereby placing the second switching device in a second open state;
applying the external energy to the patient, thereby inducing a voltage on the second electrical terminal, wherein the induced voltage is at a level that is prevented from conducting current through the second switching device when in the second open state that would otherwise be conducted through the second switching device when in the first open state.

19. The method of claim 18, further comprising conveying a series of stimulation pulses between first and second electrodes via the first and second electrical terminals, thereby creating a charge in tissue adjacent the first electrode, wherein the relatively high voltage is applied to the first and second switching devices during the conveyance of each of the pulses, and the first and second switching devices are grounded to place the first and second switching devices into a closed state after the conveyance of each of the pulses, thereby recovering the charge from the tissue.

20. The method of claim 14, wherein the relatively low voltage is less than five volts, and the relatively high voltage is greater than ten volts.

21. The method of claim 14, further comprising transmitting a signal to the neurostimulation device when the neurostimulation device is in the standby mode, wherein the relatively high voltage is applied to the first switching device in response to the transmitted signal.

22. The method of claim 21, further comprising, in response to the signal, preventing the neurostimulation device from being deactivated in the presence of the external energy.

23. The method of claim 22, wherein the neurostimulation device includes a sensing mechanism configured for deactivating the neurostimulation device in the presence of the external energy, wherein the neurostimulation device is prevented from being deactivated by disabling the sensing mechanism.

24. The method of claim 14, wherein the neurostimulation device is implanted within the patient.

\* \* \* \* \*